US012310401B2

(12) United States Patent
Kleine-Wächter et al.

(10) Patent No.: US 12,310,401 B2
(45) Date of Patent: May 27, 2025

(54) VAPORIZER CARTRIDGE AND INHALER COMPRISING SUCH A VAPORIZER CARTRIDGE

(71) Applicant: KÖRBER TECHNOLOGIES GMBH, Hamburg (DE)

(72) Inventors: Michael Kleine-Wächter, Lankau (DE); Lennart Kock, Hamburg (DE)

(73) Assignee: Körber Technologies GmbH, Hamburg (DE)

( * ) Notice: Subject to any disclaimer, the term of this patent is extended or adjusted under 35 U.S.C. 154(b) by 390 days.

(21) Appl. No.: 17/640,658

(22) PCT Filed: Sep. 7, 2020

(86) PCT No.: PCT/EP2020/074906
§ 371 (c)(1),
(2) Date: Mar. 4, 2022

(87) PCT Pub. No.: WO2021/048039
PCT Pub. Date: Mar. 18, 2021

(65) Prior Publication Data
US 2022/0378098 A1  Dec. 1, 2022

(30) Foreign Application Priority Data

Sep. 11, 2019  (DE) .......................... 102019124411.0

(51) Int. Cl.
*A24F 40/42* (2020.01)
*A24F 7/00* (2006.01)
(Continued)

(52) U.S. Cl.
CPC ................ *A24F 40/42* (2020.01); *A24F 7/00* (2013.01); *A24F 40/10* (2020.01); *A24F 40/44* (2020.01); *A24F 40/485* (2020.01); *A61M 15/06* (2013.01)

(58) Field of Classification Search
None
See application file for complete search history.

(56) References Cited

U.S. PATENT DOCUMENTS 9,986,769 B1    6/2018  Liu et al.
2015/0245666 A1  9/2015  Memari et al.
(Continued)

FOREIGN PATENT DOCUMENTS

CN    110089778 A     8/2019
DE   102017123868 A1  4/2019
(Continued)

OTHER PUBLICATIONS

International Search Report dated Dec. 4, 2020; International Applicaiton PCT/EP2020/074906.

*Primary Examiner* — Katherine A Will
(74) *Attorney, Agent, or Firm* — Dinsmore & Shohl LLP (57) ABSTRACT

A vaporizer cartridge of an inhaler has a liquid storage tank and a hollow body with a continuous air flow channel. The storage tank has an access opening to the air flow channel. A vaporizer unit extends over the entire access opening and is arranged in the region of the access opening. The vaporizer unit has a wick member towards the storage tank and a heating member towards the air flow channel. The vaporizer unit is liquid-permeable such that liquid is conveyed at least initially from the tank through the vaporizer unit to the channel in a capillary manner. The interior of the tank is structurally divided into fluidically coupled main and auxiliary volume. Only the auxiliary volume is in direct contact with the vaporizer unit, such that the liquid from the main volume contacts the wick member solely via the auxiliary volume. An inhaler may include the vaporizer cartridge.

16 Claims, 7 Drawing Sheets

(51) Int. Cl.
  *A24F 40/10*    (2020.01)
  *A24F 40/44*    (2020.01)
  *A24F 40/485*   (2020.01)
  *A61M 15/06*    (2006.01)

(56)         References Cited

U.S. PATENT DOCUMENTS

2018/0098575 A1*  4/2018  Liu .................... A61M 11/042
2018/0184712 A1   7/2018  Fraser et al.
2019/0166911 A1   6/2019  Xu et al.
2019/0208821 A1   7/2019  Fraser et al.
2019/0246696 A1   8/2019  Schmidt et al.
2021/0195952 A1   7/2021  Trieu et al.
2022/0354172 A1* 11/2022  Bergmann ............ A61M 15/06

FOREIGN PATENT DOCUMENTS

DE    102018100949 A1   7/2019
EP         3407677 A1  11/2018
WO      2018083007 A1   5/2018

* cited by examiner

VAPORIZER CARTRIDGE AND INHALER COMPRISING SUCH A VAPORIZER CARTRIDGE

CROSS-REFERENCE TO RELATED APPLICATIONS

This application is the U.S. National Stage of PCT/EP2020/074906 filed on Sep. 7, 2020, which claims priority to German Patent Application 102019124411.0 filed on Sep. 11, 2019, the entire content of both are incorporated herein by reference in their entirety.

FIELD OF THE INVENTION

The invention relates to a vaporizer cartridge as part of an inhaler, comprising at least one storage tank for receiving and storing a liquid and at least one hollow body with a continuous air flow channel, wherein the storage tank has at least one access opening to the air flow channel, and a vaporizer unit which extends over the entire access opening is arranged in the region of each access opening, said vaporizer unit having a wick member directed towards the storage tank and a heating member directed towards the air flow channel, the vaporizer unit being configured to be liquid-permeable such that liquid can be conveyed out of the storage tank through the vaporizer unit in the direction of the air flow channel in a capillary manner at least initially.

In addition, the invention relates to an inhaler configured and adapted for inhaling vapour enriched with active ingredients, comprising a cartridge carrier comprising at least one control unit and an energy source, as well as a vaporizer cartridge.

BACKGROUND OF THE INVENTION

Such vaporizer cartridges and inhalers are used in the luxury goods/stimulants industry, here in particular in connection with an electronic cigarette, the so-called e-cigarette, as well as in the medical field to enable the inhalation of fluid tobacco products and/or fluid medical products in vapour form and/or as aerosols. During consumption, a person usually sucks on a mouthpiece of the inhaler which creates a suction pressure in the air flow channel and creates an air flow through the air flow channel. The airflow, however, can also be generated mechanically, e.g. by a pump. A vaporized liquid provided by the vaporizer unit is added to the airflow in the air flow channel to administer an aerosol or aerosol-vapour mixture to the consumer. The liquid is stored on or in the vaporizer cartridge. Various mixtures with different constituents of the same or different vapour densities are used as the liquid. A typical mixture for use in an e-cigarette has, for example, constituents of glycerine and propylene glycol, possibly enriched with nicotine and/or almost any other flavourings. For use in the medical or therapeutic field, e.g. for inhaling asthma preparations, the mixture may have appropriate medical constituents and active ingredients.

The individual parts of the vaporizer cartridge, namely the storage tank, the hollow body and the vaporizer unit, may be combined in a common component, this component then being a single-use item designed for a finite number of inhalation puffs by a consumer and forming an inhaler, together with a cartridge carrier as a multi-use item which comprises at least one electronic control unit and an energy source. The vaporizer cartridge, however, may also first be formed by assembling a plurality of components, with individual components, namely the hollow body and the vaporizer unit in particular, being arranged in the cartridge carrier as a multi-use item, and the storage tank as a separate component forming the single-use item. Ultimately, the inhaler may be used variably by replacing the single-use item which usually contains the liquid.

Accordingly, the single-use item and the multi-use item are releasably connected to each other. The cartridge carrier as a multi-use item usually comprises at least one electronic control unit and an energy source. The energy source, for example, may be a disposable electrochemical battery or a rechargeable electrochemical battery, e.g. a Li-ion battery, by means of which the heating member is supplied with energy via electrical contacts of the vaporizer unit. The electronic and/or electrical control unit is used to control the vaporizer unit inside the vaporizer cartridge. The cartridge carrier, however, may also include parts of the vaporizer cartridge. The single-use item may be configured as a plug-in part which can be plugged into the multi-use item or as an insertable part which can be inserted into the multi-use item. Screw connections, snap-in connections or other quick-release connections can also be used instead of a plug-in connection. By connecting single-use item and multi-use item, a mechanical and electrical coupling is established to create a ready-for-use inhaler.

The central component which ultimately determines use (e.g. as e-cigarette or as medical inhaler) is the storage tank as part of the vaporizer cartridge. This cartridge usually contains the storage tank with a liquid selected, desired and/or required by the person or a liquid mixture (also generally referred to below as fluid) as well as the hollow body forming the flow channel and the vaporizer unit. The fluid is stored in the storage tank of the vaporizer cartridge. By means of the liquid-permeable vaporizer unit, the fluid is conveyed out of the storage tank through the wick member and the heating member due at least initially to capillary transport. The voltage generated by an energy source and applied to the heating member results in a current flow in the heating member which is preferably a planar and flat MEMS device (micro-electro-mechanical system device), e.g. consisting substantially of silicon or comprising silicon or p- or n-doped silicon. Due to the heating resistance, preferably the ohmic resistance of the heating member, the current flow leads to heating of the heating member and ultimately to vaporization of the fluid located in the vaporizer unit. The vapour and/or aerosol generated in this way escape from the vaporizer unit in the direction of the air flow channel and are mixed with the air flow as a vapour addition. The fluid thus has a predetermined path with a predetermined flow direction, namely as fluid through the wick member to and through the heating member and in vapour form from the heating member into the air flow channel. In the air flow channel, the vaporized fluid is entrained by the air flow, forming vapour/mist and/or aerosol when a pressure or negative pressure is admitted to the air flow channel by, for example, a consumer sucking on the air flow channel or a pump conveying an air flow through the air flow channel.

So that the fluid from the storage tank does not flow directly into the air flow channel, the vaporizer unit completely covers the access from the storage tank to the air flow channel. In this context, completely covers means that the liquid is forcibly conducted through the vaporizer unit so that the fluid cannot enter the air flow channel directly from the storage tank but must take the "detour" via the wick member and the heating member. On the one hand, the wick member is used for the temporary storage of fluid so as to provide sufficient fluid for a few puffs on the inhaler, particularly when the storage tank is almost empty. On the other hand, the wick member is used in particular to transport the fluid from the storage tank in the direction of the heating member and at the same time acts as a kind of non-return protection to prevent fluid and/or gas or vapour from flowing back in the direction of the storage tank as well as to prevent individual constituents of the fluid from accumulating at higher temperatures.

The known vaporizer cartridges have the disadvantage that the volume of liquid temporarily stored is limited by the—very restricted—volume of the wick member. The result of this is that liquid can only be vaporized via the heating member as long as liquid is present in the wick member. When the liquid temporarily stored in the wick member has completely vaporized, the heating member adjacent to the wick member heats without being wetted with liquid, resulting in a so-called dry puff. A dry puff can lead to increased pollutant values in the air flow of the air flow channel and significantly reduce the functionality and the lifetime of the heating member. Furthermore, a dry puff can also generate an undesirable change in taste because of the "burnt" liquid.

Accordingly, the wick member needs to be continuously supplied or permanently wetted with liquid from the storage tank. In known vaporizer cartridges, however, supplying the wick member with liquid from the storage tank depends heavily on the spatial orientation of the vaporizer cartridge and in particular of the storage tank. The wick member is configured and aligned with the storage tank namely in such a way that the wick member is only in direct contact with the liquid when the storage tank is completely full. Conversely, this means that the wick member is not in contact with the liquid in all spatial orientations of the vaporizer cartridge and in particular of the storage tank, when the storage tank is at least partially empty, for example when the wick member is above the level of the liquid in the storage tank. This constellation means that a continuous supply of the wick member is interrupted, at least temporarily, especially as the heating member—due to the very small temporary storage volume of the wick member—can also only be supplied with liquid from the wick member to a very limited extent, with the adverse effect of the dry puff described. In summary, supplying the wick member with liquid from the storage tank is position-dependent and thus discontinuous.

SUMMARY OF THE INVENTION

The object of the invention is thus to propose a vaporizer cartridge which is easy and inexpensive to produce and which ensures a continuous and reliable supply of liquid to the wick member to prevent so-called dry puff events, irrespective of the spatial orientation of the vaporizer cartridge. The object further consists of creating a corresponding inhaler.

This object is achieved by a vaporizer cartridge of the type referred to hereinbefore in that the interior of the storage tank is structurally divided into a main volume and at least one auxiliary volume, the main volume and the auxiliary volume being fluidically coupled together and only the auxiliary volume being in direct contact with the vaporizer unit in such a manner that liquid from the main volume can be brought into contact with the wick member solely and necessarily via the auxiliary volume. The main volume is a receiving chamber which is spatially bounded on all sides. The auxiliary volume—with the exception of the fluid coupling—is a receiving chamber which is spatially bounded on all sides and is preferably smaller than the main volume. Fluidically coupled within the meaning of the invention means that liquid can be exchanged between the main volume and the auxiliary volume. Direct contact within the meaning of the invention means that the wick member, as part of the vaporizer unit, is shielded as it were from the main volume by the auxiliary volume such that liquid from the main volume can only reach the wick member via the auxiliary volume. Correspondingly, the main volume is only in direct contact with the wick member. Ultimately, the wick member is located in the auxiliary volume, such that the wick member is evenly and continuously supplied with liquid regardless of the location/position/orientation (=spatial orientation) of the storage tank and input of the main volume. Even with a spatial orientation of the vaporizer cartridge in which the wick member is above the liquid level of the main volume, the wick member is supplied with liquid from the auxiliary volume, preventing the heating member from drying up. The fact that only the auxiliary volume is in direct contact with the wick member ensures that the wick member is supplied regardless of the spatial orientation of the main volume of the storage tank, effectively preventing dry puff events. Incidentally, the auxiliary volume increases the—only very restricted—storage volume of the wick member so that, even when the main volume is empty, an improved and longer supply of liquid to the wick member is ensured for additional inhalation puffs.

The inside of the storage tank is preferably divided by a separating wall or similar into the main volume and at least one auxiliary volume, the auxiliary volume being in fluid connection with the main volume for receiving liquid therefrom. Separating wall within the meaning of the invention is any structural component which is suitable for dividing the internal volume of the storage tank into two separate chambers. The chambers are interconnected by at least one opening such that liquid from the main volume can flow into the auxiliary volume directed towards the wick member and can be temporarily stored in the auxiliary volume to supply the wick member continuously with liquid. As a result, the heating member can also be supplied with liquid more reliably and independently of the main volume and its spatial orientation. When filling the vaporizer cartridge and during normal handling of the vaporizer cartridge, in particular as part of the inhaler, e.g. by tilting, swivelling or rotating, liquid passes from the main volume via the or each opening into the auxiliary volume from which the wick member is supplied.

A preferred development of the vaporizer cartridge is characterised in that the auxiliary volume forms a temporary reservoir and establishes fluid connection between the main volume and the wick member of the vaporizer unit. The temporary reservoir stores a supply of liquid in close proximity to the wick member thus ensuring that it is supplied with liquid or wetted regardless of the fill level of the main volume. The auxiliary volume forms a kind of through-chamber for the liquid so that the wick member is in fluid connection with the liquid from the main volume via the auxiliary volume.

Expediently, the temporary reservoir shields the wick member from the main volume with the exception of at least one access opening for establishing fluid connection between the auxiliary volume and the main volume. Shielding within the meaning of the invention means that the liquid from the main volume has no direct access to the wick member but must necessarily take the path via the auxiliary volume.

A preferred embodiment of the vaporizer cartridge is characterised in that it comprises a tank shell for forming the main volume of the storage tank, an adaptor forming a receiving chamber for forming the auxiliary volume of the storage tank as a temporary reservoir within the main volume, as well as a channel element as a hollow body forming the air flow channel or parts thereof. The tank shell, adaptor and channel element may be produced and formed integrally, for example by injection moulding or similar. A one-piece format enables particularly easy and inexpensive production. The said components, however, may also be configured separately, the components then being joined together, for example by means of interference fits.

Advantageously, the vaporizer cartridge comprises a carrier element which, on the one hand, has a through-channel for forming the air flow channel or parts thereof and, on the other hand, has a recess for receiving the vaporizer unit, wherein the carrier element and the vaporizer unit form a structural unit which is arranged inside the receiving chamber of the adaptor in a sealing manner with respect to the environment. This preferably prefabricated structural unit is easy to assemble as a kind of plug-in element, the structural unit with the adaptor being insertable into the tank shell in particular before the storage tank is filled with the liquid. As a result, the storage tank is at least partially closed even before filling, so that protection against contaminants exists in the storage tank.

Preferably, the auxiliary volume forming the temporary reservoir is defined by the inner surface of the receiving chamber of the adaptor directed away from the main volume of the storage tank and the outer surface of the structural unit formed by the vaporizer unit and the carrier element, wherein the inner surface of the receiving chamber of the adaptor is configured and adapted to form the auxiliary volume at least partially spaced apart from the outer surface of the structural unit. This forms an intermediate space in which the liquid can be stored. The adaptor, for example, may have a pot-shaped configuration, the structural unit being located inside the adaptor so that the wick member is permanently and directly in contact with the liquid in the temporary reservoir.

In a preferred embodiment, the carrier element and the channel element form a continuous vent with the air flow channel through the vaporizer cartridge, the carrier element and the channel element being connected to each other in a sealing manner. The sealing connection may be made, for example, by means of a one-piece configuration. Preferably, however, the carrier element and the channel element are separate components which are inserted into or pushed onto each other. A channel-like section of the carrier element is inserted into the channel element, a sealing element being arranged between the channel-like section of the carrier element and the channel element. Optionally, the channel-like section of the carrier element can also be pushed onto the channel element or be otherwise connected to it in a sealing manner.

Particularly preferably, at least one riser, which starts from the auxiliary volume and protrudes into the main volume to form a fluid connection, is configured and arranged. Fluid connection between the main volume and the auxiliary volume can be established by means of a riser. The riser may represent the only fluid connection. However, the riser may also optimise the fluid connection in addition to other openings, holes, gaps, etc. so that the temporary reservoir is reliably supplied with liquid from the main volume.

Expediently, a free end of the riser comprising at least one flow channel for receiving liquid from the main volume is configured at a distance from the tank shell of the storage tank which defines the main volume. The distance between the free end of the riser and the tank shell or other boundaries of the storage tank creates a gap or access for filling the riser. A plurality of risers which open into the temporary reservoir in different regions can also be provided. Each riser can also have more than one flow channel to keep the feed rate of liquid from the main volume into the auxiliary volume at a constantly high level.

Particularly preferably, arranged within the flow channel of the riser is a valve element which, on the one hand, enables the inflow of liquid from the main volume into the auxiliary volume and, on the other hand, at least impedes or completely prevents an outflow of liquid from the auxiliary volume into the main volume. For example, a ball valve may be arranged in the flow channel that holds the ball in the closed position, e.g. by gravity alone or by means of a spring element, to prevent a backflow of liquid from the auxiliary volume into the main volume, the ball being pressed out of the closed position by gravity and/or by the liquid flowing out of the main volume such that liquid can flow from the main volume into the auxiliary volume or into the temporary reservoir.

Advantageously, each riser is oriented substantially parallel to the air flow channel. This orientation ensures a particularly effective supply of liquid into the temporary reservoir.

An advantageous development of the vaporizer cartridge is characterised in that the tubular tank shell has an end face on the mouthpiece side and an end face on the base side, both end faces being closed by a cover element in a sealing manner, at least one cover element being releasably fastened to the tank shell for filling the storage tank. On the one hand, this ensures pre-assembly of the vaporizer cartridge and, on the other hand, easy filling of the storage tank with liquid. The sealing connection between cover element and tank shell can be achieved by a one-piece configuration/production or by sealing elements, such as simple O-rings or the like.

Particularly preferably, the cover element arranged on the base side is releasably connected to the tank shell. This configuration makes it particularly easy to fill the storage tank with liquid from the base side. Separate covers may be used as cover elements. In other embodiments, the cover element may also be formed by flange-like sections of the carrier element and/or adaptor. Ultimately, however, the mouthpiece-side cover element or both the base-side cover element and the mouthpiece-side cover element may be releasably fastened to the tank shell.

Advantageously, the mouthpiece-side cover element is formed integrally with the tank shell, wherein the mouthpiece-side cover element is formed as a mouthpiece. As a result, it is possible to dispense with gaps, joining seams, glued joints or the like which enables improved usage properties, particularly in light of the fact that for sucking, the mouthpiece is placed in the mouth of the person using the vaporizer cartridge. However, multi-part embodiments in which the components are glued or lasered, for example, are also possible in principle.

Particularly preferably, the adaptor has micro-holes and/or micro-openings, and/or forms them together with the tank shell and/or the channel element and/or the cover elements, through which liquid can be conveyed from the main volume into the auxiliary volume. The ensures an optimised supply of the liquid into the auxiliary volume. In particular, micro-openings/micro-gaps, etc. are created without additional effort during the production/manufacture of the individual components. On the contrary, it is even possible to produce more cost-efficiently as the components can be produced with larger tolerances—and therefore more cheaply—which then leads to the gap dimensions through which liquid can flow/creep into the auxiliary volume.

Advantageously, the auxiliary volume is at least partially filled with a liquid-storing material, preferably with granular grains. This optimises the storage volume in close proximity to the wick member. Ultimately, the auxiliary volume, which is partially or completely filled with non-woven material and/or foam material and/or fibrous material and/or the granular grains and/or other liquid-storing material or material mixtures, forms a kind of extension/enlargement of the wick member, thus achieving greater independence when the main volume is supplying the wick member, and without limiting or impeding the ability to fill the tank volume.

The object is also achieved by an inhaler of the type referred to hereinbefore in that the vaporizer cartridge is configured and adapted as described herein.

The advantages arising from this have already been described in connection with the vaporizer cartridge, which is why reference will be made to the preceding statements to avoid repetitions.

BRIEF DESCRIPTION OF THE DRAWINGS

Further expedient and/or advantageous features and developments of the vaporizer cartridge and the inhaler emerge from the description. Especially preferred embodiments of the vaporizer cartridge and the inhaler are explained in greater detail with reference to the associated drawing. The drawing shows.

DETAILED DESCRIPTION OF THE INVENTION

The vaporizer cartridge shown in the drawing acts as part of an inhaler for inhaling vapour and/or aerosols of liquids enriched with active ingredients, e.g. nicotine, and accordingly is described in connection with an e-cigarette. The vaporizer cartridge and the inhaler can be used in the same way for inhaling vapour, enriched with medical active ingredients, from pharmaceutical and/or dietary supplement products.

The vaporizer cartridge 10 shown forms a part of an inhaler 11. For this purpose, the vaporizer cartridge 10 is configured and adapted for mechanical and electrical connection to a cartridge carrier 14 comprising at least one electronic control unit 12 and an energy source 13, wherein electrical contacts 15 lead from the vaporizer cartridge 10 to the cartridge carrier 14 for contacting electrically with the energy source 13 (see FIG. 1 in particular). The inhaler 11, for example, may be activated by a person inhaling, for example as an e-cigarette, by the person sucking on a mouthpiece 16 or may be activated by a pump, for example, as a medical instrument, for example, in the event that the person can no longer suck or cannot suck sufficiently.

The vaporizer cartridge 10 as part of an inhaler 11 shown in FIGS. 2 to 5, comprises at least one storage tank 17 for receiving and storing a liquid 18 and at least one hollow body 19 with a continuous air flow channel 20, wherein the storage tank 17 has at least one access opening 21 to the air flow channel 20, and a vaporizer unit 22 which extends over the entire access opening 21 is arranged in the region of each access opening 21, said vaporizer unit having a wick member 23 directed towards the storage tank 17 and a heating member 24 directed towards the air flow channel 20, the vaporizer unit 22 being configured to be liquid-permeable such that the liquid 18 can be conveyed out of the storage tank 17 through the vaporizer unit 22 in the direction of the air flow channel 20 in a capillary manner at least initially.

The hollow body 19 with its at least one air flow channel 20, two or more air flow channels 20 may also be provided, forms a suction channel/vent. The shape of the hollow body 19 can be almost arbitrary, as can the course of the air flow channel 20. What is crucial is that an inlet side $E_s$ of each air flow channel 20 is open to the environment, for example to allow air to be drawn in, and that an outlet side $A_s$ is open, for example, to allow a negative pressure to be created, in particular due to the sucking of a consumer. Open in this context means that the inlet side E and the outlet side $A_s$ are permeable to air. In the region of the access opening 21 between storage tank 17 and air flow channel 20, the vaporizer unit 22 forms a kind of liquid barrier which prevents liquid 18 from flowing from the storage tank 17 directly and as liquid 18 into the air flow channel 20. Regardless of the shape and configuration of the storage tank 17, two or more storage tanks 17 may also be provided, and of the hollow body 19 and of the arrangement/positioning of storage tank 17 to hollow body 19, the vaporizer unit 22 ensures that liquid 18 is necessarily guided out of the storage tank 17 towards the air flow channel 20 and is discharged as gas or vapour into the air flow channel 20 at the latest when it exits from the vaporizer unit 22.

This vaporizer cartridge 10 is characterised according to the invention in that the interior of the storage tank 17 is structurally divided into a main volume 25 and at least one auxiliary volume 26, the main volume 25 and the auxiliary volume 26 being fluidically coupled together and only the auxiliary volume 26 being in direct contact with the vaporizer unit 22, in such a manner that liquid 18 from the main volume 25 can be brought into contact with the wick member 23 solely and necessarily via the auxiliary volume 26.

On passing through the vaporizer unit 22 comprising the wick member 23 and the heating member 24, vapour and/or aerosol is formed from the liquid 18 of the storage tank 17 towards the air flow channel 20 during operation of the vaporizer cartridge 10, the porous structure of the wick member 23 having micro-channels and/or micro-openings, the wick member 23, for example, as a fibre wick formed from a plurality of interwoven/twisted threads/fibres, e.g. made of cotton or glass fibres, may be configured as a one-piece wick block consisting of ceramic materials, or as a wick member formed from granular grains, on the one hand forming a storage medium for liquid 18 and, on the other hand, representing a flow resistor. The flow direction of the liquid 18 is from the storage tank 17 through the vaporizer unit 22 towards the air flow channel 20.

The vaporizer cartridge 10 according to the invention, as a single-use item, may be a structural unit that contains the components of storage tank 17, hollow body 19 and vaporizer unit 22. The vaporizer cartridge 10 may also be configured in multiple parts, the components of the vaporizer cartridge 10 being distributed between the single-use item and the multi-use item in such a manner that the storage tank 17, for example, is a single-use item that only results in the structural unit of the vaporizer cartridge 10 when it is brought together with a cartridge carrier 14, which may be a multi-use item and, in addition to the electronic control unit 12 and the energy source 13, may also comprise components of the vaporizer cartridge 10, such as the hollow body 19 and the vaporizer unit 22. Accordingly, the vaporizer cartridge 10 is defined by its components, namely storage tank 17, hollow body 19 with air flow channel 20, and vaporizer unit 22, and not by the constructional/structural assignment of the components to the multi-use or single-use item.

When taken on their own or in combination with each other, the features and developments described below illustrate preferred embodiments. It is expressly pointed out that features which are summarised in the claims and/or the description and/or the drawing or are described in a common embodiment can also further develop the vaporizer cartridge 10 described above in a functionally independent manner.

As in all preferred embodiments of the vaporizer cartridge 10 illustrated according to FIGS. 2 to 5, the interior of the storage tank 17 is divided by a separating wall 27 or similar into the main volume 25 and at least one auxiliary volume 26, the auxiliary volume 26 being in fluid connection with the main volume 25 for receiving liquid 18 therefrom. A pot-shaped element which, on the one hand, is connected to the hollow body 19 and, on the other hand, completely surrounds the vaporizer unit 22 at least radially, preferably serves as a separating wall 27. However, elements or components of a different design may be used as a separating wall 27 which, on the one hand, prevent the liquid 18 from being fed directly from the main volume 25 to the vaporizer unit 22 and, specifically, to the wick member 23 and, on the other hand, form a receiving chamber for receiving the liquid 18. The auxiliary volume 26 forms a temporary reservoir for the liquid 18 and establishes a fluid connection between the main volume 25 and the wick member 23 of the vaporizer unit 22. The temporary reservoir shields the wick member 23 from the main volume 25 with the exception of at least one access opening 28 for establishing fluid connection between the auxiliary volume 26 and the main volume 25 (see, for example, FIG. 2). In individual embodiments, a single access opening 28 may be configured. Preferably, however, a plurality of access openings 28 is provided. Further examples are described in detail below for this purpose.

Optionally and preferably, the vaporizer cartridge 10 comprises a tank shell 29 for forming the main volume 25 of the storage tank 17, an adaptor 31 forming a receiving chamber 30 for forming the auxiliary volume 26 of the storage tank 17 as a temporary reservoir within the main volume 25, as well as a channel element 32 as a hollow body 19 forming the air flow channel 20 or parts thereof. Particularly preferably, the tank shell 29 forms a cylindrical, tubular body, it being possible for the configuration of the outer and inner shape of the body to deviate in a like manner to its cross-sectional shape. The body formed by the tank shell 29 has two end faces, namely an end face B on the base side and an end face M on the mouthpiece side which are closed in a sealing manner by cover elements 33 or the like such that the liquid 18 is securely stored inside the storage tank 17. The adaptor 31, as separating wall 27 for structurally creating the temporary reservoir, may be configured as a separate component. In this case, the adaptor 31 is pushed onto or into the channel element 32 (see FIGS. 2, 4 and 5 for example). The adaptor 31, however, may also be formed integrally with the channel element 32 (see FIG. 3 for example). The adaptor 31 elongates the channel element 32 towards end face B on the base side which, in particular when filling the storage tank 17 from end face B on the base side, means that a higher filling level can be achieved in the storage tank 17. In the preferred embodiments, the channel element 32 itself, which may extend through the entire storage tank 17, only extends through a portion of the storage tank 17, starting from end face M on the mouthpiece side. For example, the channel element 32, the course and cross-section of which may vary, is a simple tube.

The vaporizer cartridge 10 preferably further comprises a carrier element 34 which, on the one hand, has a through-channel 35 for forming the air flow channel 20 or parts thereof and, on the other hand, has a recess 36 for receiving the vaporizer unit 22, the carrier element 34 and the vaporizer unit 22 forming a structural unit which is arranged inside the receiving chamber 30 of the adaptor 31 in a sealing manner with respect to the environment. This unit, which is also referred to as the inside vaporizer unit, is arranged, on the one hand, at least partially, but in any case with the entire vaporizer unit 22, inside the receiving chamber 30 of the adaptor 31 and, on the other hand, is connected to the channel element 32. The carrier element 34 and the channel element 32 form a continuous vent 37 with the air flow channel 20 through the whole vaporizer cartridge 10, the carrier element 34 and the channel element 32 being connected to each other in a sealing manner. The sealing connection may be made, for example, by means of a one-piece configuration. Optionally, however, the carrier element 34 and the channel element 32 are separate components which are inserted into or pushed onto each other. A channel-like section 38 of the carrier element 34 is inserted into the channel element 32, a sealing element 39, for example in the form of a simple O-ring, being arranged between the channel-like section 38 of the carrier element 34 and the channel element 32. Optionally, the channel-like section 38 of the carrier element 34 may also be pushed onto the channel element 32 or be otherwise connected to it.

In the embodiments shown, the auxiliary volume 26 forming the temporary reservoir is defined by the inner surface I of the receiving chamber 30 of the adaptor 31 directed away from the main volume 25 of the storage tank 17 and the outer surface A of the structural unit formed by the vaporizer unit 22 and the carrier element 34, the inner surface I of the receiving chamber 30 of the adaptor 31 being configured and adapted to form the auxiliary volume 26 at least partially spaced apart from the outer surface A of the structural unit. The liquid 18 passes from the main volume 25 through the or each access opening 28 into the auxiliary volume 26 and is temporarily stored therein. In the embodiment according to FIG. 2, an access opening 28 is configured in the wall of the adaptor 31. In addition to this, liquid 18 can also pass into the auxiliary volume 26 through assembly fits/interference fits, for example in the contact region between the free edge area 40 of the adaptor 31 and the carrier element 34 and/or in the plug-in area 41 between adaptor 31 and channel element 32 (see FIG. 2, for example). In other embodiments (see FIG. 5, for example), at least one intake 42 may be configured in the free edge area 40 which may be arranged at a distance from an end-face cover element 33. Alternatively or cumulatively, for example, micro-openings 43 or the like may be configured in the peripheral wall of the adaptor 31 which assist in feeding liquid 18 into the auxiliary volume 26.

Figure 3:
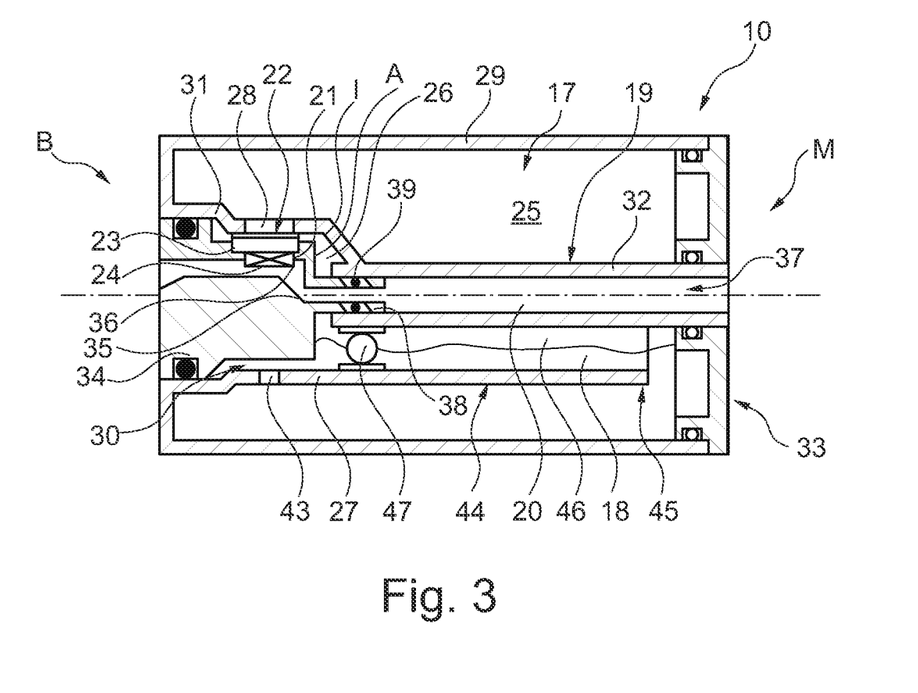
FIG. 3 is a view of a further embodiment of a vaporizer cartridge according to the invention.

Likewise alternatively or cumulatively, in preferred embodiments of the vaporizer cartridge 10, at least one riser 44, which starts from the auxiliary volume 26 and protrudes into the main volume 25 to form a fluid connection, is configured and arranged (see, e.g. FIG. 3). A free end 45 of the riser 44 comprising at least one flow channel 46 for receiving liquid 18 from the main volume 25 is configured at a distance from the tank shell 29 or a cover element 33 of the storage tank 17 which defines the main volume 25. Two or more flow channels 46 may also be configured inside the riser 44. Two or more risers 44 may also be arranged to establish a fluid connection between main volume 25 and auxiliary volume 26. Optionally, arranged within the flow channel 46 of the riser 44 is a valve element 47 or the like which, on the one hand, enables the inflow of liquid 18 from the main volume 25 into the auxiliary volume 26 and, on the other hand, at least impedes an outflow of liquid 18 from the auxiliary volume 26 into the main volume 25. The course and/or orientation of the riser 44 or of the flow channel 46 formed therein may vary. Preferably, each riser 44 or the flow channel 46 is oriented substantially parallel to the air flow channel 20.

Figure 2:
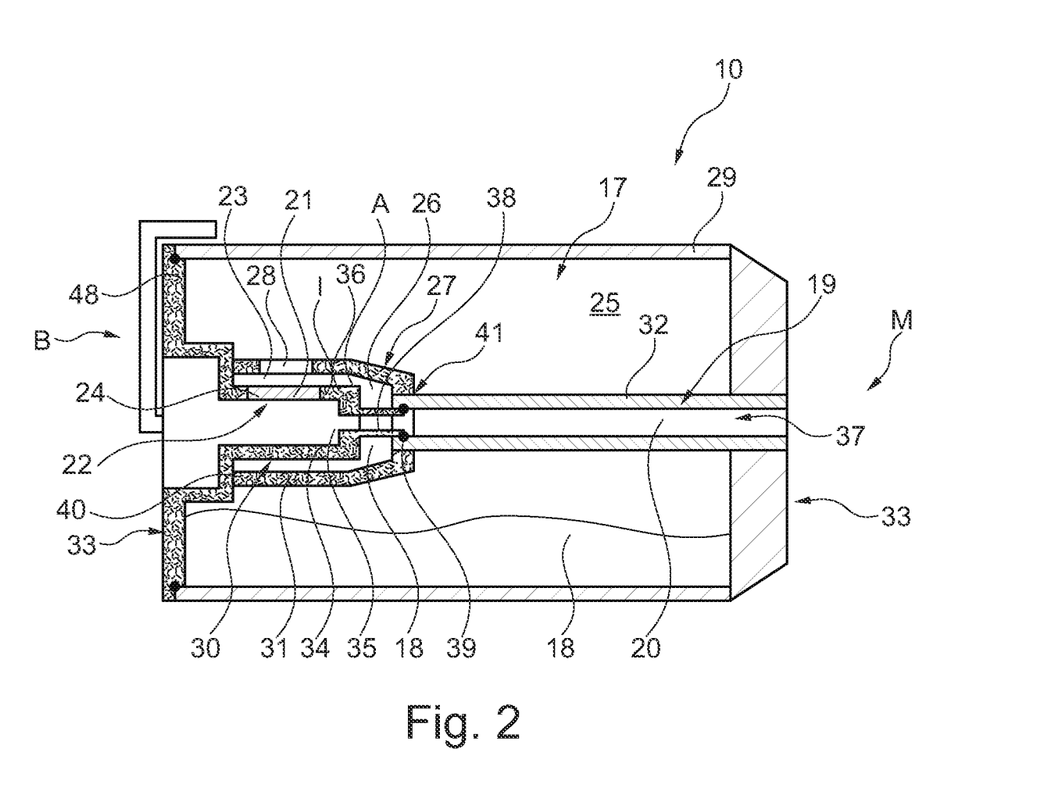
FIG. 2 is a view of a first embodiment of a vaporizer cartridge according to the invention in section.

In the embodiment according to FIG. 2, the tank shell 29 and the mouthpiece-side cover element 33 are formed integrally. The adaptor 31, the channel element 32 and the carrier element 34 are separate components. The adaptor 31 is pushed onto and fastened to a free end of the channel element 32 which end is directed towards end face B on the base side, forming an assembly fit/interference fit. The carrier element 34 with the vaporizer unit 22 is positioned in sections, namely with the section having the vaporizer unit 22, in the receiving chamber 30 of the adaptor 31, in such a manner that the wick member 23 is in the region of the access opening 28. The channel-like section 38 of the carrier element 34 is connected to the channel element 32 in a sealing manner, e.g. by means of a simple O-ring, and fastened thereto. The carrier element 34 further comprises a flange-like collar 48 such that the carrier element 34 forms the releasable cover element 33 on the end face B on the base side. The flange-like collar 48 of the carrier element 34 is connected to the tank shell 29 in a sealing manner, e.g. by means of a simple O-ring. Electrical contacts 15 for connection to the energy source 13 are associated with the heating member 24.

The embodiment according to FIG. 3 shows a vaporizer cartridge 10 in which the tank shell 29, the adaptor 31, the channel element 32 and the riser 44 are integrally formed and produced, for example by injection moulding. The carrier element 34 with the vaporizer unit 22 is arranged entirely inside the receiving chamber 30 of the adaptor 31, which is configured open to end face B on the base side, in such a manner that the wick member 23 is positioned in the region of the access opening 28. The channel-like section 38 of the carrier element 34 is connected to the channel element 32 in a sealing manner, e.g. by means of a simple O-ring, and fastened thereto. The carrier element 34 is further configured to seal towards the environment, e.g. by means of a simple O-ring, with respect to the inner surface I of the receiving chamber 30 and thus forms the cover element 33 as it were on end face B on the base side. On end face M on the mouthpiece side, the storage tank 17 is closed by a releasable cover element 33, the cover element 33 being config-ured to seal both to the tank shell 29 and to the channel element 32, e.g. by means of simple O-rings.

Figure 4:
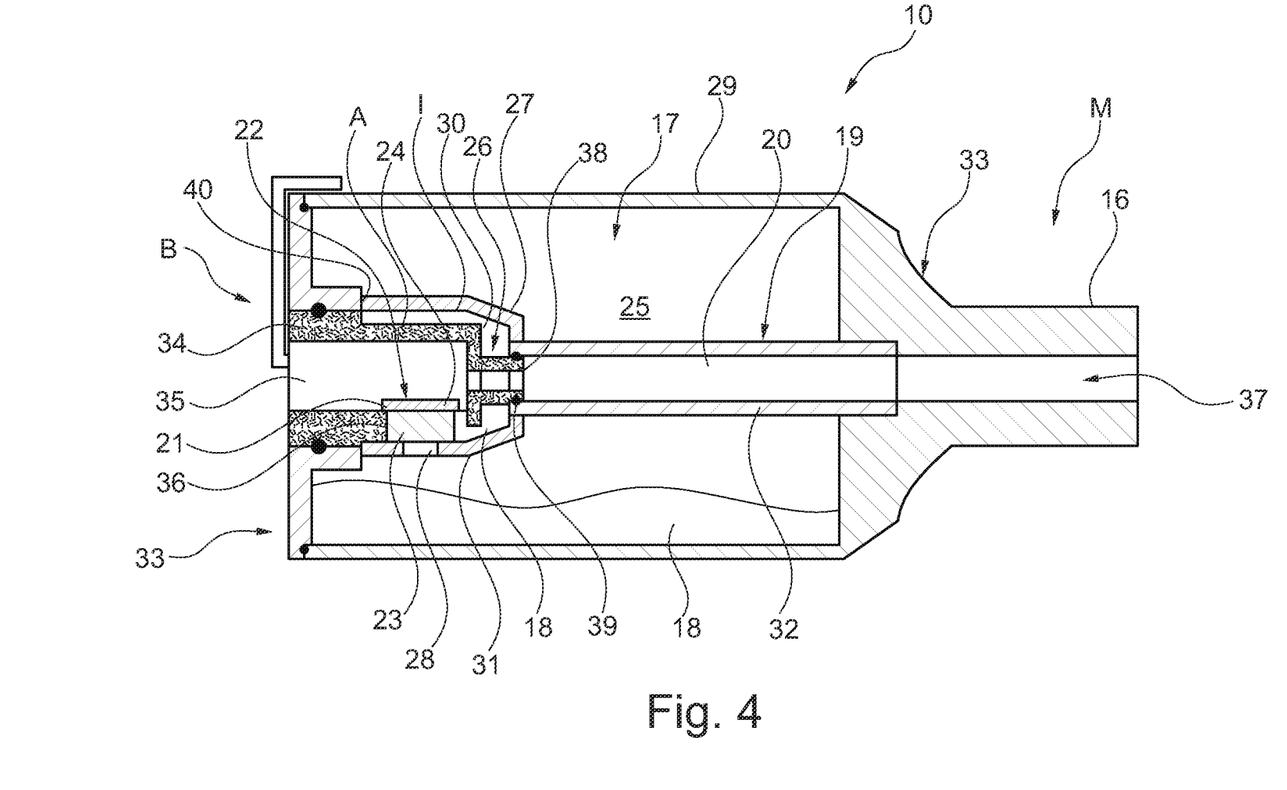
FIG. 4 is a view of a further embodiment of a vaporizer cartridge according to the invention.

In the vaporizer cartridge 10 according to FIG. 4, the tank shell 29 and the mouthpiece-side cover element 33 are formed integrally. The adaptor 31, the channel element 32 and the carrier element 34 are separate components. The adaptor 31 is pushed onto and fastened to a free end of the channel element 32 which end is directed towards end face B on the base side, forming an assembly fit/interference fit. The carrier element 34 with the vaporizer unit 22 is positioned in sections, namely with the section having the vaporizer unit 22, in the receiving chamber 30 of the adaptor 31, in such a manner that the wick member 23 is in the region of the access opening 28. The channel-like section 38 of the carrier element 34 is connected to the channel element 32 in a sealing manner, e.g. by means of a simple O-ring, and fastened thereto. The storage tank 17 is closed on the end face B on the base side with a releasably fastened cover element 33, the cover element 33 being configured, on the one hand, to seal with respect to the carrier element 34, for example by means of a simple O-ring, and being configured, on the other hand, to seal with respect to the tank shell 29, for example by means of a simple O-ring. In the embodiment according to FIG. 4, the mouthpiece-side cover element 33 is not only integrally formed with the tank shell 29, the mouthpiece-side cover element 33 is also shaped as mouthpiece 16 for being sucked by a person.

Figure 5:
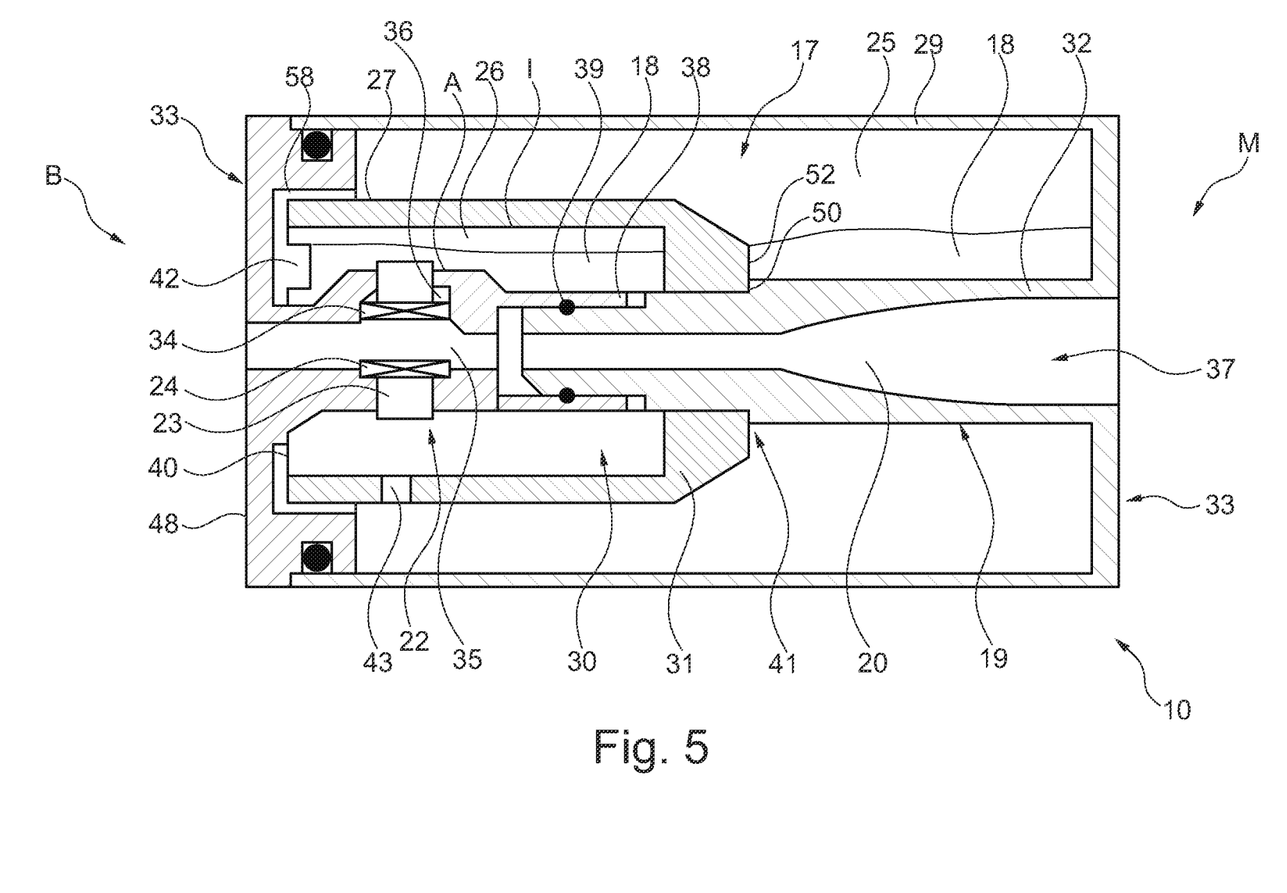
FIG. 5 is a view of a further embodiment of a vaporizer cartridge according to the invention.

In the vaporizer cartridge 10 according to FIG. 5, the tank shell 29 and the mouthpiece-side cover element 33 are also integrally formed, the channel element 32 additional being formed integrally with the tank shell 29 and the cover element 33. The adaptor 31 and the carrier element 34 are separate components. The adaptor 31 is fitted against a ledge 50 on the outer surface of the channel element 32, the ledge 50 determining the position for the adaptor 31. The carrier element 34 with the vaporizer unit 22 is positioned in sections, namely with the section having the vaporizer unit 22, in the receiving chamber 30 of the adaptor 31. The wick member 23 is formed radially surrounding the carrier element 34 such that the wick member 23 is located with at least one section at the lowest position of the auxiliary volume 26 in any orientation of the vaporizer cartridge 10. A heating member 24 may be provided. Optionally, for example, two heating members 24 may also be provided. The heating member 24 may also be formed and arranged circumferentially. The overflow 42 is configured as access opening 28. In addition, one or a plurality of micro-openings 43 are configured in the circumferential surface of the adaptor 31. The channel-like section 38 of the carrier element 34 is connected to the channel element 32 in a sealing manner, e.g. by means of a simple O-ring, and fastened thereto. The storage tank 17 is closed on end face B on the base side with a releasably fastened cover element 33, the cover element 33 being formed by the flange-like collar 48 of the carrier element 34. The flange-like collar 48 of the carrier element 34 is connected to the tank shell 29 in a sealing manner, e.g. by means of a simple O-ring. On the one hand, the free edge area 40 of the adaptor 31 is at a distance from the cover element 33. On the other hand, at least a gap 58 is formed between the radially directed outer surface of the adaptor 31 and the cover element 33 to create access for the liquid 18 into the auxiliary volume 26.

The auxiliary volume 26 may be at least partially filled with a liquid-storing material, preferably with granular grains. The entire auxiliary volume 26 if preferably filled, for example, by non-woven material or foam material or fibrous material or granular grains expanding the wick member 23. Instead of the O-rings described throughout as sealing elements, other common seals can also be used. The embodiments illustrated which do not have a riser 44 may, of course, be supplemented with such.

Figure 6:
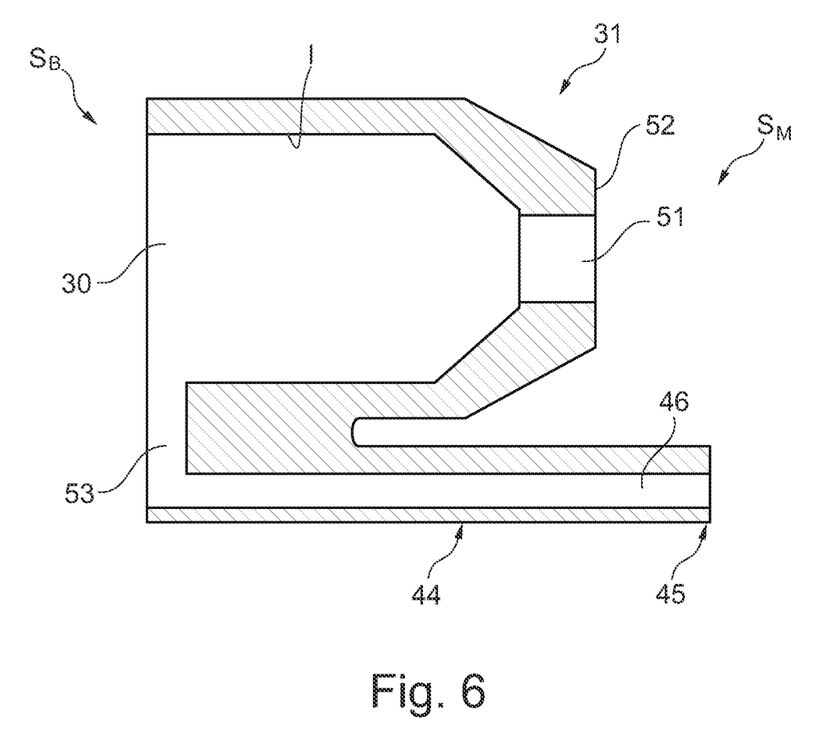
FIG. 6 is a view of a further embodiment of an adaptor for a vaporizer cartridge according to the invention.
Figure 7:
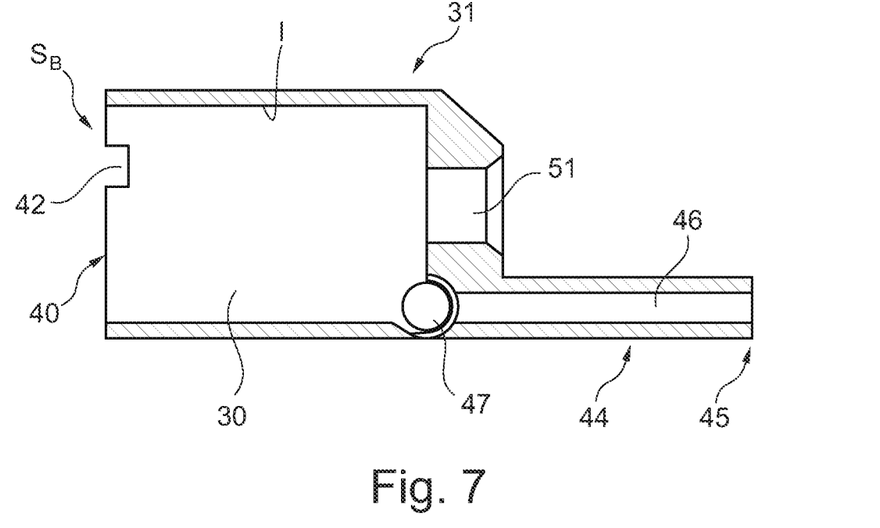
FIG. 7 is a view of a further embodiment of an adaptor for a vaporizer cartridge according to the invention.
Figure 8:
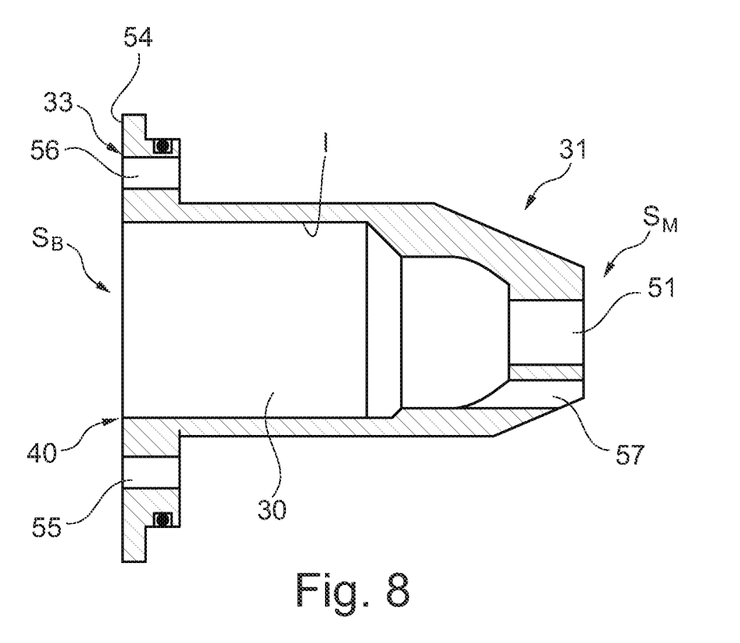
FIG. 8 is a view of a further embodiment of an adaptor for a vaporizer cartridge according to the invention.

FIGS. 6 and 8 illustrate further embodiments of the adaptor 31 which can be integrated into all the aforementioned vaporizer cartridges 10. The adaptor 31 according to FIG. 6 is formed integrally with a riser 44. The adaptor 31 has a through-hole 51 on the side SM on the mouthpiece side into which the channel element 32 can be inserted. The end face itself forms an abutment 52 for the assembly position on the channel element 32. A material reduction 53 which forms an intake/overflow for the fluid 18 from the riser 44 into the receiving chamber 30 is configured on the side SB on the base side. The adaptor 31 according to FIG. 7 is similarly configured. However, the intake 42 is formed on the free edge are 40 of the adaptor 31. The valve element 47 is arranged in the riser 44 in the transition region to the receiving chamber. The adaptor 31 according to FIG. 8 has a flange-like section 54, in such a manner that this section 54 forms the base-side cover element 33 which can be releasably and sealingly connected to the tank shell 29, for example by means of a simple O-ring. A closable fill opening 55 and a closable vent opening 56 are configured in the flange-like section 54. In addition, next to the through-hole 51 for receiving the channel element 32, the adaptor 31 has, on the side SM on the mouthpiece side, a through-hole 57 for receiving a riser 44. The advantage of the adaptor 31 according to FIG. 8 is that the entire vaporizer cartridge 10 can be pre-assembled and has an almost completely closed storage tank 17 when the liquid 18 is filled via the fill opening 55, with the result that there is a significantly reduced risk of contaminating the liquid 18 in the storage tank 17.

The assembly of a vaporizer cartridge 10, in which the liquid 18 is filled into the storage tank 17 from end face B on the base side, is described by way of example with reference to FIG. 5. First, the tank shell 29 is produced and provided integrally with the channel element 32. Then the adaptor 31 is inserted into the base-side open end of the storage tank 17 and positioned and then fastened by means of the abutment 52, which abuts against the ledge 50. The positioning ensures the formation of a gap in the free edge area 40 of the adaptor 31. Then the liquid 18 is poured into the storage tank, at most up to the upper edge of the free edge area 40. The adaptor 31 can significantly increase the filling level of the liquid 18 as the adaptor 31 elongates as it were the channel element 32 towards end face B on the base side. Subsequently, the carrier element 34 is assembled with the vaporizer unit 22 as a unit, the flange-like collar 48 of the carrier element 34 acting as cover element 33 and closing the storage tank 17 If the vaporizer cartridge 10 has an adaptor 31 according to FIG. 8, the entire vaporizer cartridge 10 is first assembled before the liquid 18 is fed in.

The assembly of a vaporizer cartridge 10 in which the liquid 18 is filled from end face M on the mouthpiece side is described by way of example with reference to FIG. 3. First, the component comprising the tank shell 29, the adaptor 31, the channel element 32 and the riser 44 is produced and provided integrally. Subsequently, the unit formed by carrier element 34 and vaporizer unit 22 is installed in the adaptor 31. Then the storage tank 17 is filled with the liquid 18 via end face M on the mouthpiece side. After filling, end face M on the mouthpiece side M is closed in a sealing manner by means of the cover element 33.

Figure 1:
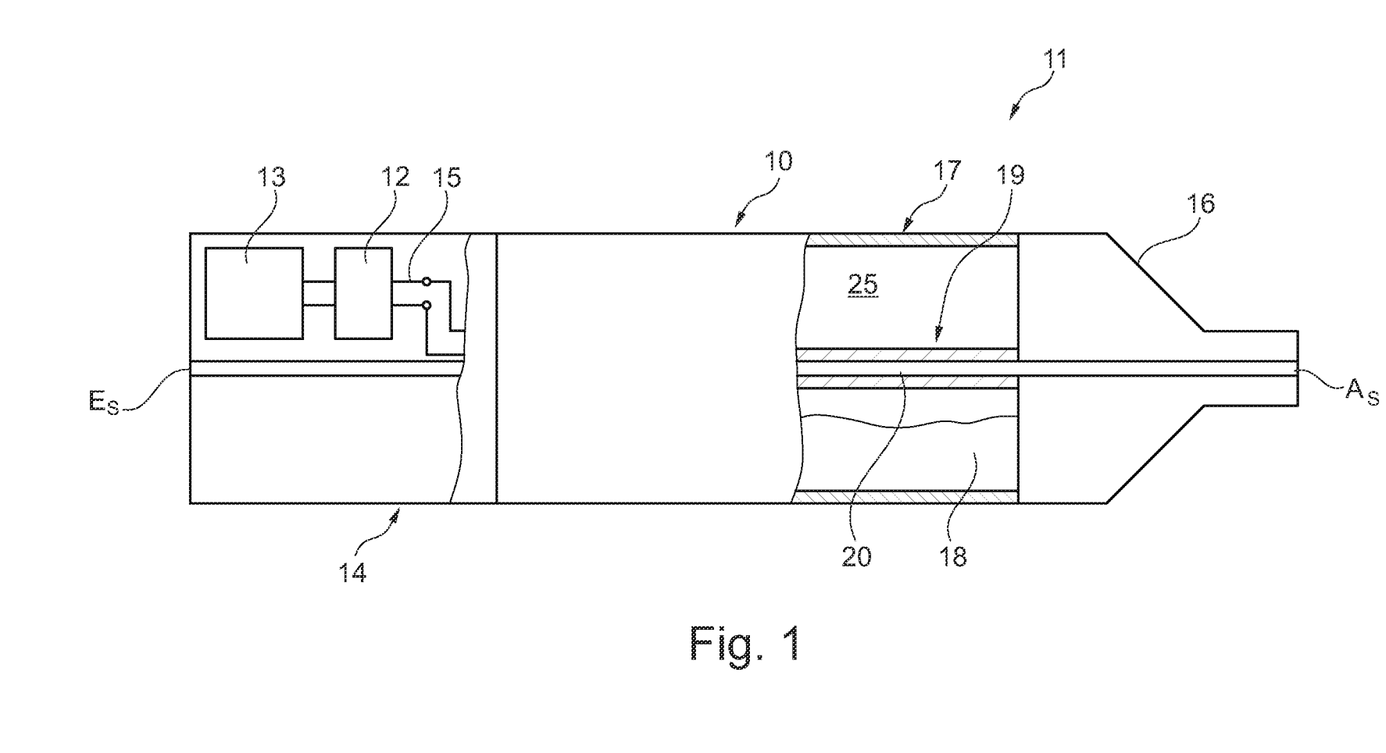
FIG. 1 is a schematic illustration of a preferred embodiment of an inhaler according to the invention with cartridge carrier and vaporizer cartridge in partial section.

The operating principle of the inhaler 11 according to the invention, which comprises a vaporizer cartridge 10 according to the invention, is described by way of example with reference to an e-cigarette as inhaler 11, in particular with reference to FIG. 1. A consumer sucks, for example, on a mouthpiece 16 of the inhaler 11 which is formed from the cartridge carrier 14 and the vaporizer cartridge 10, a liquid 18 being located in the storage tank 17 of the vaporizer cartridge 10 which contains, for example, glycerine, propylene glycol and possibly other active ingredients and/or flavourings. Sucking creates a negative pressure in the air flow channel 20, which in turn activates the control unit 12, for example via a sensor that is not shown. The control unit 12 controls the heating member 24 which is supplied with energy by the energy source 13. Initially at least, liquid 18 from the storage tank 17 is transported by means of the wick member 23 out of the storage tank 17 through microchannels in a capillary manner, namely by the wick member 23 from the main volume 25 via the auxiliary volume 26 towards the heating member 24. On or in the heated heating member 24, the liquid 18 is converted into gas or vapour, the heating member 24 transporting the liquid 18 or the gas or the vapour formed therefrom towards the air flow channel 20 and delivering it thereto due to the gas- or vapour-permeable structure. The gas leaving the heating member 24 mixes with the air flow in the air flow channel 20, wherein the actual recondensation/vapour formation process occurs, and is sucked in and inhaled by the consumer.

Due to the auxiliary volume 26, even when the main volume 25 is emptying or has emptied, a residue of liquid 18 is still stored temporarily and in close proximity and in contact with the wick member 23 such that a further continuous supply of the wick member 23 with liquid 18 is ensured at least for several inhalation puffs or vaporization processes.

The invention claimed is:

1. A vaporizer cartridge as part of an inhaler, comprising:
at least one storage tank for receiving and storing a liquid;
at least one hollow body with a continuous air flow channel;
the storage tank having an access opening to the air flow channel;
a vaporizer unit extending over an entirety of the access opening and arranged in a region of the access opening, said vaporizer unit having a wick member directed towards the storage tank and a heating member directed towards the air flow channel, wherein the vaporizer unit is liquid-permeable such that the liquid is at least initially conveyed out of the storage tank through the vaporizer unit in a direction of the air flow channel in a capillary manner;
wherein an interior of the storage tank is structurally divided into a main volume and at least one auxiliary volume, the main volume and the auxiliary volume being fluidically coupled together, and only the auxiliary volume being in direct contact with the vaporizer unit such that the liquid from the main volume is brought into contact with the wick member solely and necessarily via the auxiliary volume, wherein the wick occupies only a portion of the auxiliary volume; and
wherein the interior of the storage tank is divided by a separating wall into the main volume and the at least one auxiliary volume, wherein the auxiliary volume is in fluid connection with the main volume for receiving liquid therefrom; and further comprising:
a tank shell forming the main volume of the storage tank;
an adaptor forming a receiving chamber for forming the auxiliary volume of the storage tank as a temporary reservoir within the main volume;

a channel element as a hollow body forming the air flow channel or parts thereof; and at least one riser starting from the auxiliary volume and protruding into the main volume to form a fluid connection.

2. A vaporizer cartridge according to claim 1, wherein the auxiliary volume forms the temporary reservoir and establishes a fluid connection between the main volume and the wick member of the vaporizer unit.

3. A vaporizer cartridge according to claim 2, wherein the temporary reservoir shields the wick member from the main volume with the exception of at least one access opening establishing the fluid connection between the auxiliary volume and the main volume.

4. A vaporizer cartridge according to claim 1, further comprising:
a carrier element having a through-channel for forming the air flow channel or parts thereof and a recess for receiving the vaporizer unit;
wherein the carrier element and the vaporizer unit form a structural unit which is arranged inside the receiving chamber of the adaptor in a sealing manner with respect to the environment.

5. A vaporizer cartridge according to claim 4, wherein the auxiliary volume forming the temporary reservoir is defined by an inner surface of the receiving chamber of the adaptor directed away from the main volume of the storage tank and an outer surface of the structural unit formed by the vaporizer unit and the carrier element, wherein the inner surface of the receiving chamber of the adaptor is configured and adapted to form the auxiliary volume at least partially spaced apart from the outer surface of the structural unit.

6. A vaporizer cartridge according to claim 4, wherein the carrier element and the channel element form a continuous vent with the air flow channel through a whole of the vaporizer cartridge, the carrier element and the channel element being connected to each other in a sealing manner.

7. A vaporizer cartridge according to claim 1, wherein a free end of the riser comprises at least one flow channel for receiving liquid from the main volume and is configured at a distance from the tank shell of the storage tank which defines the main volume.

8. A vaporizer cartridge according to claim 7, further comprising a valve element arranged within the flow channel of the riser, wherein the valve element enables an inflow of liquid from the main volume into the auxiliary volume and impedes an outflow of liquid from the auxiliary volume into the main volume.

9. A vaporizer cartridge according to claim 1, wherein each of the at least one riser is oriented substantially parallel to the air flow channel.

10. A vaporizer cartridge according to claim 1, wherein the tank shell has an end face on a mouthpiece side and an end face on a base side, both end faces being closed by a cover element in a sealing manner, at least one of the cover elements being releasably fastened to the tank shell for filling the storage tank.

11. A vaporizer cartridge according to claim 10, wherein the cover element arranged on the base side is releasably connected to the tank shell.

12. A vaporizer cartridge according to claim 10, wherein the mouthpiece-side cover element is formed integrally with the tank shell and the mouthpiece-side cover element is shaped as a mouthpiece.

13. A vaporizer cartridge according to claim 10, wherein the adaptor has and/or, together with the tank shell and/or the cover elements, forms micro-holes and/or micro-openings through which liquid is conveyed from the main volume into the auxiliary volume.

14. A vaporizer cartridge according to claim 1, wherein the auxiliary volume is filled at least partially with a liquid-storing material.

15. A vaporizer cartridge according to claim 14, wherein the liquid-storing material is granular grains.

16. An inhaler, configured and adapted for inhaling vapour enriched with active ingredients, comprising:
at least one electronic control unit;
a cartridge carrier comprising an energy source; and
a vaporizer cartridge according to claim 1.

* * * * *